United States Patent [19]
Mandai et al.

[11] Patent Number: 5,922,691
[45] Date of Patent: *Jul. 13, 1999

[54] CRYSTALLINE MALTOTETRAOSYL GLUCOSIDE, AND ITS PRODUCTION AND USE

[75] Inventors: Takahiko Mandai; Takashi Shibuya; Toshiyuki Sugimoto; Toshio Miyake, all of Okayama, Japan

[73] Assignee: Kabushiki Kaisha Hayashibara Seibutsu Kagaku Kenkyujo, Okayama, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/826,765

[22] Filed: Apr. 7, 1997

Related U.S. Application Data

[63] Continuation of application No. 08/732,713, Oct. 18, 1996, abandoned, which is a continuation of application No. 08/396,748, Mar. 1, 1995, abandoned.

[30] Foreign Application Priority Data

Mar. 1, 1994 [JP] Japan ..................................... 6-054401

[51] Int. Cl.$^6$ ............................. A61K 31/715; C07H 1/00
[52] U.S. Cl. ............................. 514/54; 514/60; 536/102; 536/123.1; 536/124; 435/95; 435/96; 435/97; 435/99; 435/100; 435/101; 435/200; 435/201; 435/202
[58] Field of Search ................................. 435/95, 96, 97, 435/99, 100, 101, 200, 201, 202; 536/102, 123.1, 124; 514/54, 60

[56] References Cited

U.S. PATENT DOCUMENTS

| | | | |
|---|---|---|---|
| 4,652,640 | 3/1987 | Sakai et al. | 536/124 |
| 5,298,616 | 3/1994 | Hosang et al. | 536/118 |
| 5,455,168 | 10/1995 | Maruta et al. | 435/201 |

FOREIGN PATENT DOCUMENTS

| | | |
|---|---|---|
| 0479093 | 4/1992 | European Pat. Off. . |
| 0480640 | 4/1992 | European Pat. Off. . |
| 3529228 | 3/1986 | Germany . |
| 0023799 | 2/1983 | Japan . |
| 0148794 | 8/1984 | Japan . |
| 2106912 | 4/1983 | United Kingdom . |

OTHER PUBLICATIONS

Sucrose: Properties and Applications, M. Mathlouthi and P. Reiser Cedus, eds., Blackie Academic & Professional, an Imprint of Chapman & Hall, London 1995, pp. 138–143, month not available.

Frank H. Stodola et al, The Preparation, Properties and Structure of the Disaccharide Leucrose, Journal of American Chemical Society, vol. 78, pp. 2514–2518, Jun. 5, 1956.

Klaus Bock et al, Carbon–13 Nuclear Magnetic Resonance Data for Oligosaccharides, Advances in Carbohydrate Chemistry and Biochemistry, vol. 42, pp. 193–225, 1984.

Carbohydr. Res. (Crbrat, 00086215); 1993; vol. 242,; pp. 141–151, F. Hoffman–La Roche Ltd.,; Pharma Div.; Basel; CH–4002; Switz, month not available.

*Primary Examiner*—Kathleen K. Fonda
*Attorney, Agent, or Firm*—Browdy and Neimark

[57] ABSTRACT

Novel crystalline maltotetraosyl glucoside is obtained by crystallizing maltotetraosyl glucoside from a solution of maltotetraosyl glucoside, prepared by either exposing an aqueous solution of maltopentaose to the action of a non-reducing saccharide-forming enzyme or an aqueous solution which contains trehalose or a non-reducing saccharide to the action of cyclomaltodextrin glucanotransferase. The crystalline maltotetraosyl glucoside has non-hygroscopicity, non-reducibility, superior solubility, less fermentability, and other satisfactory properties of stabilizing oligopeptides and biologically-substances as well as preventing retrogradation of amylaceous substances. These features render the crystalline maltotetraosyl glucoside very useful in various compositions including foods, beverages, cosmetics, pharmaceuticals and shaped bodies.

19 Claims, 9 Drawing Sheets

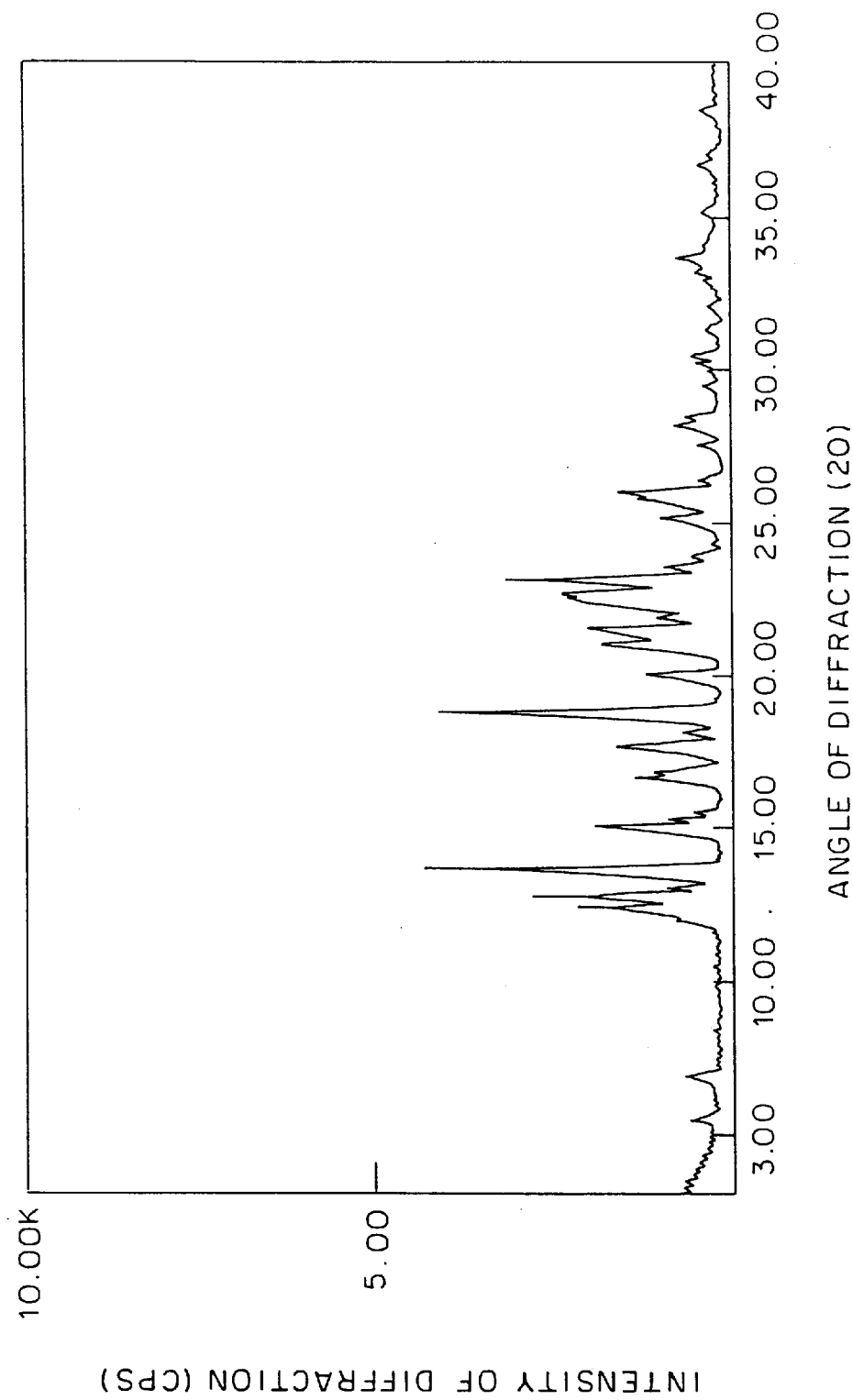

5,922,691

CRYSTALLINE MALTOTETRAOSYL GLUCOSIDE, AND ITS PRODUCTION AND USE

This application is a continuation of application Ser. No. 08/732,713 filed Oct. 18, 1996, now abandoned which is a continuation of application Ser. No. 08/396,748, filed Mar. 1, 1995, now abandoned.

BACKGROUND OF THE INVENTION

1. Field of the invention

This invention relates to a novel crystalline saccharide, and its production and use, more particularly, to a crystalline maltotetraosyl glucoside, and to its production and use.

2. Description of the prior art

Maltopentaose is a penta-saccharide represented by the general formula of O-α-D-glucopyranosyl-(1→4)-O-α-D-glucopyranosyl-(1→4)-O-α-D-glucopyranosyl-(1→4)-O-α-D-glucopyranosyl-(1→4)-D-glucopyranose, and has been known as a sweetener which is incorporated into starch syrup or its powder. This saccharide is characteristic of its low sweetness and appropriate viscosity, and used in compositions including beverages, foods and tastable products such as tobacco and cigarette. Since maltopentaose is a reducing saccharide, however, it has the drawbacks that it readily causes browning reaction along with proteins and amino acids contained in beverages and foods to induce the deterioration and degeneration of these products.

The present inventors have energetically studied means to overcome the drawbacks and found that the preparation of a non-reducing maltotetraosyl glucoside from maltopentaose is obtainable by exposing a reducing partial starch hydrolysate having a glucose polymerization degree of 3 or higher to the action of an enzyme capable of forming a non-reducing saccharide having a trehalose structure as an end unit (hereinafter called "a non-reducing saccharide-forming enzyme" in the specification), Suehas those disclosed in Japan Patent Application No.349,216/93. However, such a non-reducing saccharide of maltotetraosyl glucoside is in powdery form which is amorphous and unstable physically, and for the sake of stability the establishment of a crystalline maltotetraosyl glucoside has been desired.

OBJECT OF THE INVENTION

This invention is to establish a crystalline maltotetraosyl glucoside having non-hygroscopicity, non-reducing, superior fluidity, less fermentability and superior solubility, and to provide its production and use.

SUMMARY OF THE INVENTION

To overcome the aforementioned object, the present inventors have energetically studied. As the results, while proceeding the reaction to transform maltopentaose into a maltotetraosyl glucoside by adjusting high-purity maltopentaose to a relatively high concentrated solution of maltopenatose and exposing the resultant solution to the action of a non-reducing saccharide-forming enzyme, the present inventors found that the solution became opaque to form a precipitate, and further clarified that such a precipitate is a crystalline maltotetraosyl glucoside and accomplished this invention by establishing a novel crystalline maltotetraosyl glucoside and its production and use. In addition, the present inventors clarified that hydrous and anhydrous crystalline maltotetraosyl glucosides are present, and accomplished this invention by establishing the production of the crystalline maltotetraosyl glucoside and its uses.

BRIEF EXPLANATION OF THE FIGURES

FIG. 9 illustrates the powder X-ray diffraction figure of anhydrous crystalline maltotetraosyl glucoside.

DETAILED DESCRIPTION OF THE INVENTION

Figure 1:
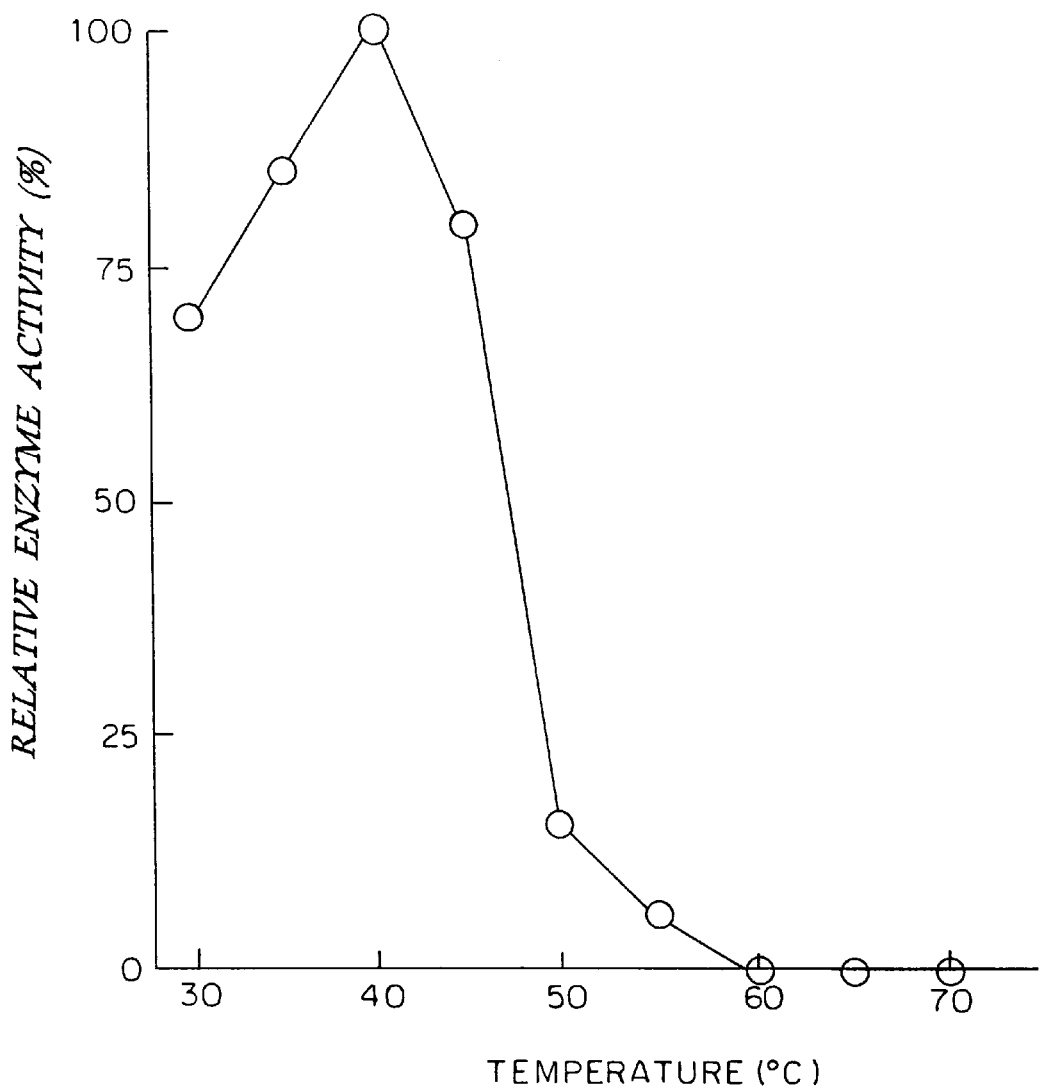
FIG. 1 illustrates the effect of temperature on the activity of a non-reducing saccharide-forming enzyme from Rhizobium M-11.
Figure 2:
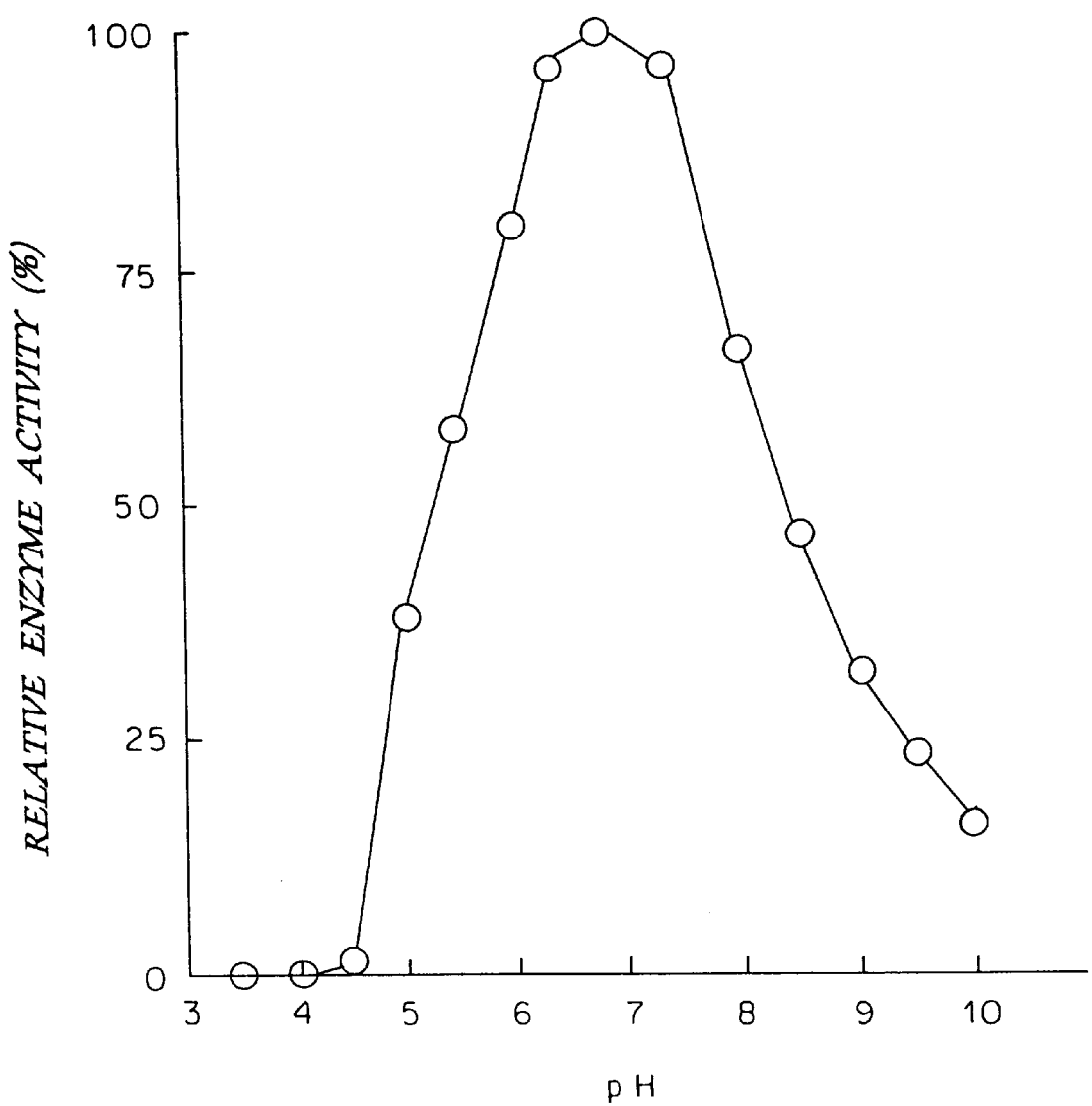
FIG. 2 illustrates the effect of pH on the activity of a non-reducing saccharide-forming enzyme from Rhizobium M-11.

Methods for preparing a crystalline maltotetraosyl glucoside feasible in this invention are those capable of forming the crystal of this invention, usually, wherein an aqueous solution of maltotetraosyl glucoside is crystallized to recover the resultant crystal, desirably, a method wherein the solution of maltotetraosyl glucoside is supersaturated and crystallized to collect the resultant crystal is favorably feasible in this invention. To prepare a maltotetraosyl glucoside, for example, a method wherein a solution of maltopentaose is allowed to act on a non-reducing saccharide-forming enzyme is feasible in this invention. As a solution of maltopentaose, a high-purity maltopentaose solution can be used, generally, such a solution of maltopentaose obtained by exposing amylaceous substance such as starch product, gelatinized starch, liquefied starch, solubilized starch, amylose, amylopectin and dextrin to the action of α-amylase or a mixture of α-amylase and a starch debranching enzyme.

Alpha-amylases usable in this invention are those having a relatively high producibility of maltopentaose, for example, "TERMAMYL 60L", α-amylase commercialized by Novo Nordisk Bioindustry, Copenhagen, Denmark, is desirably utilizable.

Starch debranching enzymes usable in this invention are those capable of separating the branch structure of amylaceous substances and elevating the producibility of maltopentaose from amylaceous substances by acting on together with α-amylase, for example, pullulanase derived from *Aerobacter aerogenes* and isoamylase derived from *Pseudomonas amyloderamosa* commercialized by Hayashibara Biochemical Laboratories, Inc., Okayama, Japan, are utilizable, in particular the co-use of isoamylase is desirable because of its specific properties.

The maltopentaose solution obtained by exposing amylaceous substances to the action of α-amylase or a mixture of α-amylase and a starch debranching enzyme, usually, contains maltopentaose in the range of 20 to 40 w/w % (the percentages as used hereinafter shall mean "w/w % on a dry solid basis" unless specified otherwise), if necessary, according to conventional separation and purification, the content of maltopentaose in such a solution can be elevated and the solution thus concentrated is favorably usable.

The non-reducing saccharide-forming enzymes usable in this invention are, for example, those disclosed in Japanese Patent Application No.349,216/93 by this inventors, Rhizobium sp M-11 and Arthrobacter sp Q36 which have been deposited in the Patent Microorganism Depository, National Institute of Bioscience and Human-technology, Agency of Industrial Science and Technology, 1–3, Higashi 1-chome, Tsukuba-shi, Ibaraki-ken, Japan, under the accession numbers of FERM BP-4130 and FERM BP-4316 respectively, and enzyme preparations obtainable by cultivating in nutrient culture media conventional microorganisms which are capable of forming non-reducing saccharides, for example, *Brevibacterium helovolum* (ATCC 11822), *Flavobacterium aquatile* (IFO 3772), *Micrococcus luteus* (IFO 3064), *Micrococcus roseus* (ATCC 186), *Curtobacterium citreum* (IFO 15231), *Mycobacterium smegmatis* (ATCC 19420) and *Terrabacter tumescens* (IFO 12960), if necessary, such enzyme preparations can be purified arbitrarily according to conventional methods prior to use.

The non-reducing saccharide enzymes thus obtained are characteristic of forming a non-reducing saccharide with a trehalose structure as an end unit from one or more members selected from the group of reducing partial starch hydrolysates having a glucose polymerization degree of 3 or higher. Any enzymatic reaction time used for allowing the non-reducing saccharide-forming enzyme to act on in this invention can be selected from the range wherein maltopentaose can be exposed to the action of such enzyme to be converted into maltotetraosyl glucoside, and the enzyme can be used arbitrarily after the use of α-amylase or a mixture of α-amylase and starch debranching enzyme, or used together with these enzymes.

Any enzymatic reaction condition can be employed in this invention as long as the enzymatic reaction proceeds, generally, a substrate concentration in the range of about 1 to 70%, a reaction temperature in the range of about 10 to 80° C., a reaction pH in the range of about 4 to 10 and a reaction time in the range of about 1 to 100 hours can be used in this invention. In such a reaction, if necessary, the enzymes can be used arbitrarily in continuous or batchwise manner when immobilized by conventional methods including carrier-binding methods, cross-linking methods and entrapping methods.

In addition to the aforementioned preparation of maltotetraosyl glucoside, the method of using a saccharide-transferring enzyme is favorably feasible in this invention, for example, a solution of maltotetraosyl glucoside is obtainable by exposing an aqueous solution which contains a mixture of trehalose and amylaceous substance or which contains non-reducing saccharide having a trehalose structure as an end unit to the action of cyclomaltodextrin glucanotransferase, or if necessary, by further allowing α-amylase or a mixture of α-amylase and starch debranching enzyme to act on after the reaction of cyclomaltodextrin glucanotransferase, it is favorably feasible in this invention to elevate the content of maltotetraosyl glucoside in such a solution.

Solutions obtained by aforementioned enzymatic reaction, usually, contains about 1 to 90% of maltotetraosyl glucoside. For producing crystalline maltotetraosyl glucoside from such solutions, generally, they are concentrated to crystallize maltotetraosyl glucoside and followed by recovering the crystal. Generally, concomitant saccharides are removed from a crude solution according to conventional manners, the resultant solution contains a high-purity maltotetraosyl glucoside, and such a solution is concentrated, followed by crystallizing maltotetraosyl glucoside and recovering the crystal.

As the above separation and purification, for example, yeast fermentation, membrane filtration, fractional sedimentation, alkali treatment and/or column chromatography are arbitrarily usable. In particular, column chromatography using a strongly-acidic cation exchanger as disclosed in Japan Patent Kokai No.23,799/83 and No.148,794/84 is favorably usable for removing concomitant saccharides and collecting fractions which are rich in maltotetraosyl glucoside. In such a chromatography, conventional fixed-bed method, moving bed method and simulated moving bed method can be used arbitrarily.

For crystallizing maltotetraosyl glucoside from the above fractions which are rich in maltotetraosyl glucoside, appropriate conditions for such a crystallization are chosen dependently on the sort of a crystalline form. The conditions for crystallization feasible in this invention are those wherein supersaturated solutions of maltotetraosyl glucoside can crystallize maltotetraosyl glucoside.

In particular, under the aforementioned conditions for crystallization, not less than about 10% of maltotetraosyl glucoside solution is concentrated to give a concentration of about 5 to 95%, and a temperature of the resultant solution lies in the range wherein the solution is not frozen and has a temperature over the melting point of crystalline maltotetraosyl glucoside and free of causing unsatisfactory browning reaction and decomposition of maltotetraosyl glucoside. For example, in the case of a hydrous crystalline maltotetraosyl glucoside, the crystallization of maltotetraosyl glucoside solutions having not less than about 5% water content is feasible at about 5 to 100° C., and in the case of an anhydrous crystalline maltotetraosyl glucoside, the crystallization of maltotetraosyl glucoside solutions having not more than about 10% water content is feasible at about 90 to 150° C. in this invention. Additionally, an anhydrous crystalline maltotetraosyl glucoside can be readily produced by drying a hydrous crystalline maltotetraosyl glucoside under reduced pressure or by drying on heat. For arranging a supersaturation degree and viscosity of maltotetraosyl glucoside solutions in the process of crystallization, ethanol, methanol and/or acetone can be used arbitrarily. Methods for crystallizing maltotetraosyl glucoside in this invention are, usually, those wherein a supersaturated solution of maltotetraosyl glucoside is adjusted to a relatively high temperature and placed in a crystallizer, if necessary, by admixing with a seed crystal in an amount of 0.1 to 5%, the resultant mixture is cooled gradually while stirring to facilitate crystallization to form a massecuit. Furthermore, since a crystalline maltotetraosyl glucoside is characteristic of readily inducing a crystallization, the continuous crystallization of maltotetraosyl glucoside wherein the solution of maltotetraosyl glucoside is concentrated continuously is favorably feasible in this invention. As methods of obtaining a crystalline maltotetraosyl glucoside from such a crystallized massecuite, for example, the conventional methods of separation, block pulverization, fluidized granulation and spray-drying are utilizable.

For example, separation methods are usually those capable of feeding massecuite to a basket-type centrifuge and separating crystals of maltotetraosyl glucoside from molasses, if necessary, such crystals can be readily washed by spraying thereto a small amount of chilled water or alcohol, and such a separation method is suitable for the production of a high-purity crystalline maltotetraosyl glucoside. Other three methods are suitable for the production of a powder containing crystalline maltotetraosyl glucoside without separating molasses because they are characteristic of elevating a yield of the production of crystalline maltotetraosyl glucoside, however the purity of crystals obtained by such three methods is not improved. Accordingly, in this invention, usually, in addition to the crystals of maltotetraosyl glucoside, oligosaccharides including maltotetraose and maltopentaose are present in material or formed in the process of production.

In the spray-drying, usually, massecuite of maltotetraosyl glucoside having a crystallinity of about 30 to 60% is sprayed from a high-pressurized pump through its nozzle, heat-dried at a high temperature that prevents the crystal of maltotetraosyl glucoside from melting, for example, at about 60 to 100° C., and aged by blowing thereto a hot air to form a crystalline maltotetraosyl glucoside powder.

In the block pulverization, usually, massecuite of maltotetraosyl glucoside having a crystallinity of about 20 to 80% is allowed to stand for about 0.5 to 3 days to crystallize and to form block, and the resultant block is subjected to pulverization or scraping, followed by drying to form a crystalline maltotetraosyl glucoside powder.

The crystalline maltotetraosyl glucoside thus obtained is substantially non-hygroscopic and free-flowing although such non hygroscopicity is varied dependently on the purity, and further readily handleable without fear of causing viscosity and solidification, and these properties reduced the material and personnel costs necessary for controlling the package, transportation and storage of crystalline maltotetraosyl glucoside. The crystalline maltotetraosyl glucoside of this invention is substantially a non or less hygroscopic powder with a relatively-high heat-resistant and stability, and it can be used as a vehicle, excipient and powder base in a powdered sweetener mixture, chocolate, chewing gum, instant juice, instant soup, granule and tablet which are obtainable by conventional manners, for example, beverages, cosmetics, pharmaceuticals, shaped bodies and other compositions, as well as in various applications such as reagent and raw material utilizable in chemical industry. Furthermore, physicochemical properties of the crystalline maltotetraosyl glucoside such as melting point and specific rotatory power are varied dependently on the purity. The melting point is lowered dependently on the decrease of the purity of maltotetraosyl glucoside and also the range is widened, and therefore a crystalline maltotetraosyl glucoside is utilizable, if necessary, by selecting arbitrarily its purity for its purpose.

The crystalline maltotetraosyl glucoside of this invention has a good sweetness. When orally administered, it is digestible and utilizable as energy sources. Furthermore, it is utilizable as a cariostatic sweetener because it is substantially not fermentable by dental caries-inducing microorganisms, and the crystalline maltotetraosyl glucoside, because of its good sweetness and usefulness as a vehicle, is favorably usable as a sugar-coating agent of tablet by using together with binders such as pullulan and/or hydroxylethyl starch. In addition, the crystalline maltotetraosyl glucoside has other properties such as body-imparting ability, moisture-retaining ability, ability preventing the crystallization of other saccharides, less fermentability, and less solubility.

These properties of the crystalline maltotetraosyl glucoside are favorably utilizable in the production of various compositions including foods, beverages, feeds, cosmetics, pharmaceuticals and shaped bodies.

The crystalline maltotetraosyl glucoside of this invention is usable intact as seasonings for sweetening. Such a crystalline maltotetraosyl glucoside, if necessary, can be used together with an appropriate amount of one or more other sweeteners, for example, powdered starch syrup, glucose, maltose, sucrose, isomerized sugar, honey, maple sugar, sorbitol, dihydrochalcone, stevioside, α-glycosyl stevioside, rebaudioside, glycyrrhizin, L-aspartyl-L-phenylalanine methyl ester, saccharin, glycine and alanine, if necessary, as well as with a filler such as dextrin, starch and lactose. In addition, it is favorably feasible in this invention to use the crystalline maltotetraosyl glucoside with an elevated solubility together with oligosaccharides such as maltotetraose and maltopentaose.

In addition, the crystalline maltotetraosyl glucoside can be used intact as a filler, vehicle or powder base, or if necessary, after admixing with other fillers, vehicles and/or binders. It can be also used by shaping into a granule, globe, short rod, plate, cube or tablet form arbitrarily.

Further the crystalline maltotetraosyl glucoside of this invention is favorably usable to sweeten foods and beverages in general as well as to improve their tastes and qualities because its taste well harmonizes with substances having other types of tastes such as sour-, salty-, astringent-, delicious- and bitter-tastes, for example, the crystalline maltotetraosyl glucoside of this invention is favorably usable in various seasonings including soy sauce, miso, vinegar, sauce, mayonnaise and "mirin (heavily sweetened sake)". In addition, the crystalline maltotetraosyl glucoside of this invention is favorably usable to sweeten various foods including Japanese-style confectioneries, Western-style confectioneries, frozen desserts, syrups, pastes, processed vegetables, pickled products, meat products, fish meat products, alcoholic drinks and beverages, and to improve their tastes and qualities.

Since the crystalline maltotetraosyl glucoside of this invention is less hygroscopic and free-flowing, for example, in the case of chewing gum, "su-konbu", candy and "gyuhi (starch paste)", the crystalline maltotetraosyl glucoside, by coating the surface of these products, is favorably utilizable as a coating material which prevents the adhesion of wrapping paper with the surface of the products or improves the sliding of wrapping paper from the surface of the products. In addition, since the crystalline maltotetraosyl glucoside of this invention is edible, relatively low soluble and heat-resistant, the crystalline maltotetraosyl glucoside is favorably usable as premixes for rice-cake coating, bun and fry coating, and as substitutes for topping and icing materials for bun and cake, and further utilizable to substitute it for powdery materials such as wheat flour, corn grits and starch in part or whole to obtain premixes for pudding, hot cake, confectioneries and bun.

Further the crystalline maltotetraosyl glucoside of this invention can be used in feeds and pet foods for domestic animals and poultries, and still further is favorably usable as a sweetener for compositions including cosmetics and pharmaceuticals such as cigarette, dentifrice, troche and internal medicine, as well as a taste improver, taste masking agent and quality improver.

The composition of this invention is a crystalline maltotetraosyl glucoside intact, or usually is prepared by mixing a crystalline maltotetraosyl glucoside together with one or more members selected from the group consisting of nutrient substances such as proteins, amino acids, fatty acids, vitamins and minerals, or pharmaceutical substances such as anti-bacterial substances, enzymes, hormones and cytokines, dependently on the uses of such compositions. If necessary, it is arbitrarily feasible to incorporate other appropriate substances into such compositions according to this invention, for example, one or more members selected from the group of taste masking agents, coloring agents, flavors, stabilizers, fillers and vehicles, and it is arbitrarily feasible to prepare the compositions thus obtained into an appropriate shape, dependently on the uses of the compositions. Methods of incorporating a crystalline maltotetraosyl glucoside into the compositions according to this invention are those which are capable of containing a crystalline maltotetraosyl glucoside before completion of their processings. For example, conventional methods such as mixing, kneading, dissolving, melting, soaking, permeating, spreading, applying, coating, spraying, injecting, crystallizing and solidifying are arbitrarily used.

The amount of the crystalline maltotetraosyl glucoside to be incorporated in these compositions is, usually, 0.1% or more, desirably, 0.2% or more, dependently on the kind of such compositions. The compositions thus obtained could find extensive uses in foods, beverages, cosmetics and pharmaceuticals which are perorally or parenterally used, as well as in domestic, agricultural, forestry, fishery, reagent and chemical industrial products.

The following experiments will explain this invention in more detail.

Experiment A explains at first the preparation, purification and characterization of a non-reducing saccharide-forming enzyme from Rhizobium sp M-11, and then illustrates the preparation of trehalose and non-reducing saccharides having a trehalose structure as an end unit from reducing partial starch hydrolysates by using such an enzyme. Experiment B explains the preparation and physicochemical properties of the crystalline maltotetraosyl glucoside of this invention.

Experiment A-1
Production of non-reducing saccharide-forming enzyme from Rhizobium sp M-11

A liquid culture medium consisting of 2.0 w/v % maltose, 0.5 w/v % peptone, 0.1 w/v % yeast extract, 0.1 w/v % disodium hydrogen phosphate, 0.1 w/v % potassium dihydrogen phosphate and water was adjusted to pH 7.0. The liquid medium was divided into 100 ml aliquots which were then placed separately in 500 ml-flasks, sterilized at 120° C. for 20 minutes in an autoclave, cooled, inoculated with Rhizobium sp M-11 (FERM BP-4130) and incubated at 27° C. for 24 hours under the stirring condition of 130 rpm, thus obtaining a seed culture.

About 20 liters of a culture medium which had the same composition as used in the seed culture was allocated in 30 liter-jar fermenter, sterilized, cooled to 30° C., inoculated with 1 v/v % of the seed culture and incubated at 30° C. and pH 6.0–8.0 for 24 hours under aeration-agitation conditions. The enzymatic activity of the resultant culture was about 1.5 units/ml. A portion of the culture was centrifugally separated into cells and supernatant and the former cells were then suspended in 50 mM phosphate buffer (ph 7.0) to give the starting volume, followed by assaying the resultant cell suspension and supernatant for enzymatic activity. As the results, the cell suspension had about 0.6 units/ml of enzymatic activity, while the supernatant had about 0.9 units/ml of enzymatic activity.

The non-reducing saccharide-forming enzyme is assayed as follows: To 4 ml of 1.25 w/v % maltopentaose as substrate (50 mM phosphate buffer, pH 7.0) is added 1 ml of an enzyme solution and the mixture is incubated at 40° C. for 60 minutes, heated at 100° C. for 10 minutes to inactivate the enzyme, correctly diluted by 10-times in deionized water and determined for reducing power by the Somogyi-Nelson method. As a control, a fresh preparation of the same enzyme solution is inactivated by heating it at 100° C. for 10 minutes and then tested similarly as above. One unit of the enzyme is defined as the amount of enzyme that diminishes 1 micromole of reducing power of maltopentaose per 1 minute under the above conditions.

Experiment A-2
Purification of enzyme

About 18 liters of the culture obtained in Experiment A-1 was treated with "MINI-LAB", a superhigh-pressure cell homogenizer (a product of Dainippon Pharmaceutical Co., Ltd., Osaka, Japan) to crush cells. The resultant was centrifuged at 10,000 rpm for 30 minutes to obtain about 16 liters of supernatant. In the supernatant was dissolved ammonium sulfate to give a saturation degree of 0.2, and the resultant solution was allowed to stand at 4° C. for 1 hour and then centrifuged at 10,000 rpm for 30 minutes to obtain a supernatant.

Additionally, in such a supernatant was dissolved ammonium sulfate to give a saturation degree of 0.6, and the resultant solution was allowed to stand at 4° C. for 24 hours and then centrifuged at 10,000 rpm for 30 minutes to collect the resultant sediment. The sediment was dissolved in 10 mM phosphate buffer (pH 7.0), dialyzed against a fresh preparation of the same buffer for 24 hours and centrifuged at 10,000 rpm for 30 minutes to remove insoluble substances. The dialyzed solution (360 ml) was divided into two portions which were then separately applied to ion exchange column chromatography using 300 ml "DEAE TOYOPEARL®", a gel of Tosoh Corporation, Tokyo, Japan.

The objective enzyme having adsorbed on DEAE TOYOPEARL®, was eluted from the column with a fresh preparation of the same phosphate buffer containing sodium chloride. The obtained enzyme-active fractions were dialyzed against a fresh preparation of the same phosphate buffer containing 2M ammonium sulfate and further centrifuged at 10,000 rpm for 30 minutes to remove insoluble substances, and the resultant supernatant was applied to hydrophobic column chromatography using 300 ml "BUTYL TOYOPEARL® 650", a gel of Tosoh Corporation, Tokyo, Japan. The enzyme having adsorbed on the column, was eluted therefrom with a linear gradient buffer decreasing from 2M to 0M, and the enzyme-active fractions were collected. In addition, the fractions were applied to gel filtration chromatography using 300 ml "TOYOPEARL®HW-55", a gel of Tosoh Corporation, Tokyo, Japan, and the enzyme-active fractions were collected. The enzymatic activities, specific activities and yields in particular purification steps were tabulated in Table 1.

TABLE 1

| Purification step | Enzyme activity (units) | Specific activity (units/mg protein) | Yield (%) |
| --- | --- | --- | --- |
| Culture | 26,800 | | 100 |
| Supernatant after cell crushing | 20,300 | 0.10 | 76 |
| Dialyzed solution after salting-out | 16,100 | 0.32 | 60 |
| Eluate from ion exchange column | 11,300 | 5.5 | 42 |
| Eluate from ion hydrophobic column | 5,730 | 98.0 | 21 |
| Eluate from gel filtration | 3,890 | 195.0 | 15 |

The purified enzyme preparation thus obtained as eluate in the gel filtration step in Table 1 was determined for its purity on electrophoresis using polyacrylamide gel (7.5 w/v %) and the electrophoresis gave a single protein band, meaning that the enzyme preparation was electrophoretically homogenous and highly pure.

Experiment A-3

Characterization of enzyme

A portion of the purified enzyme preparation obtained in Experiment A-2 was applied to electrophoresis containing 10 w/v % SDS-polyacrylamide gel and then determined for molecular weight by comparison with standard molecular markers (a product of Nippon Bio-Rad Laboratories KK, Tokyo, Japan) which had been electrophoresed on the same gel, revealing that the molecular weight of the enzyme was about 77,000–87,000 daltons.

Another portion of the purified enzyme preparation was applied to isoelectric point electrophoresis using 2 w/v % "AMPHOLINE®", a polyacrylamide gel of Pharmacia LKB, Uppscla, Sweden, and then determined for its isoelectric point by measuring pH of the electrophoresed gel, revealing that the isoelectric point of the enzyme was about 3.6–4.6.

Figure 3:
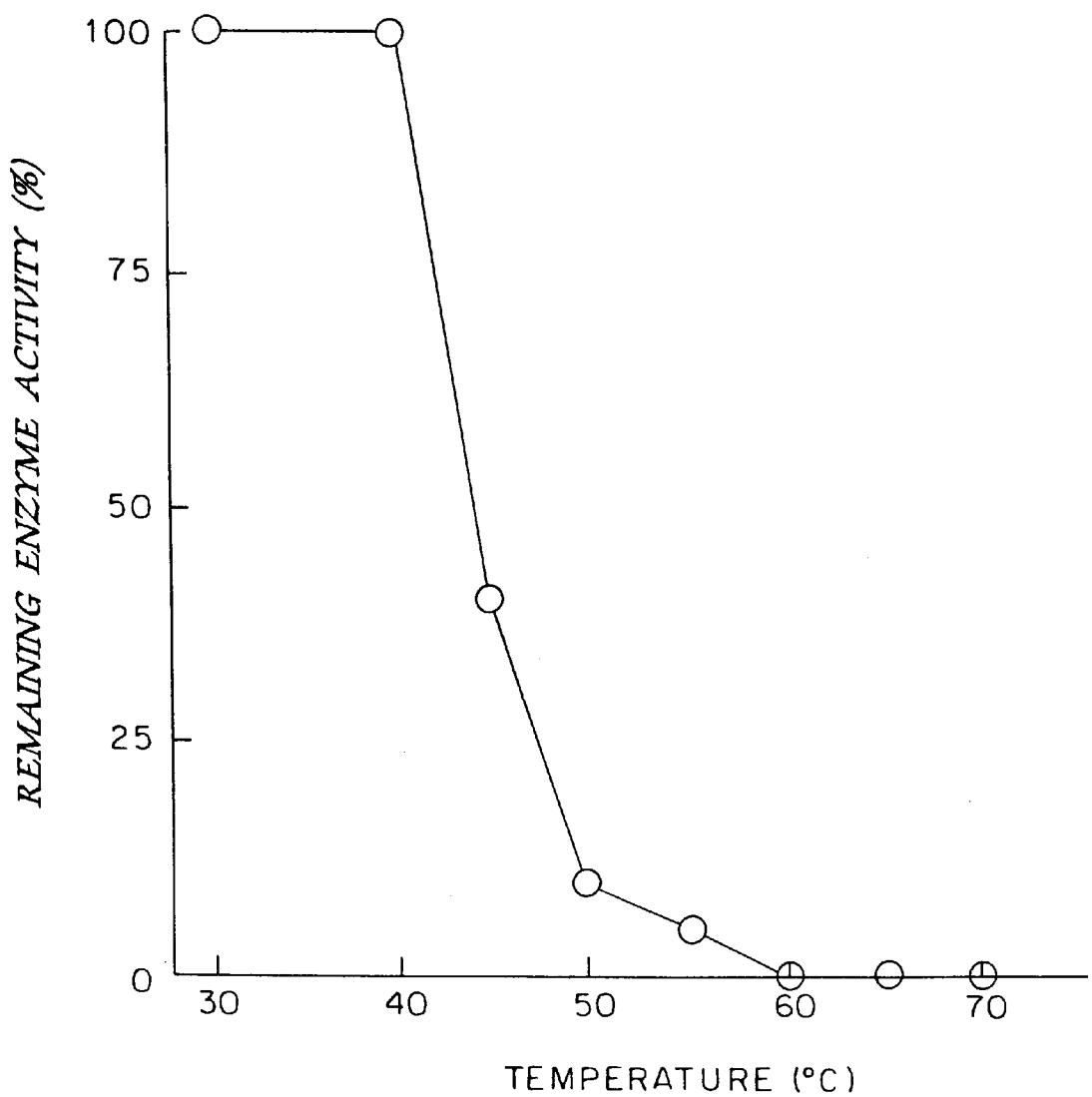
FIG. 3 illustrates the thermal stability of a non-reducing saccharide-forming enzyme from Rhizobium M-11.
Figure 4:
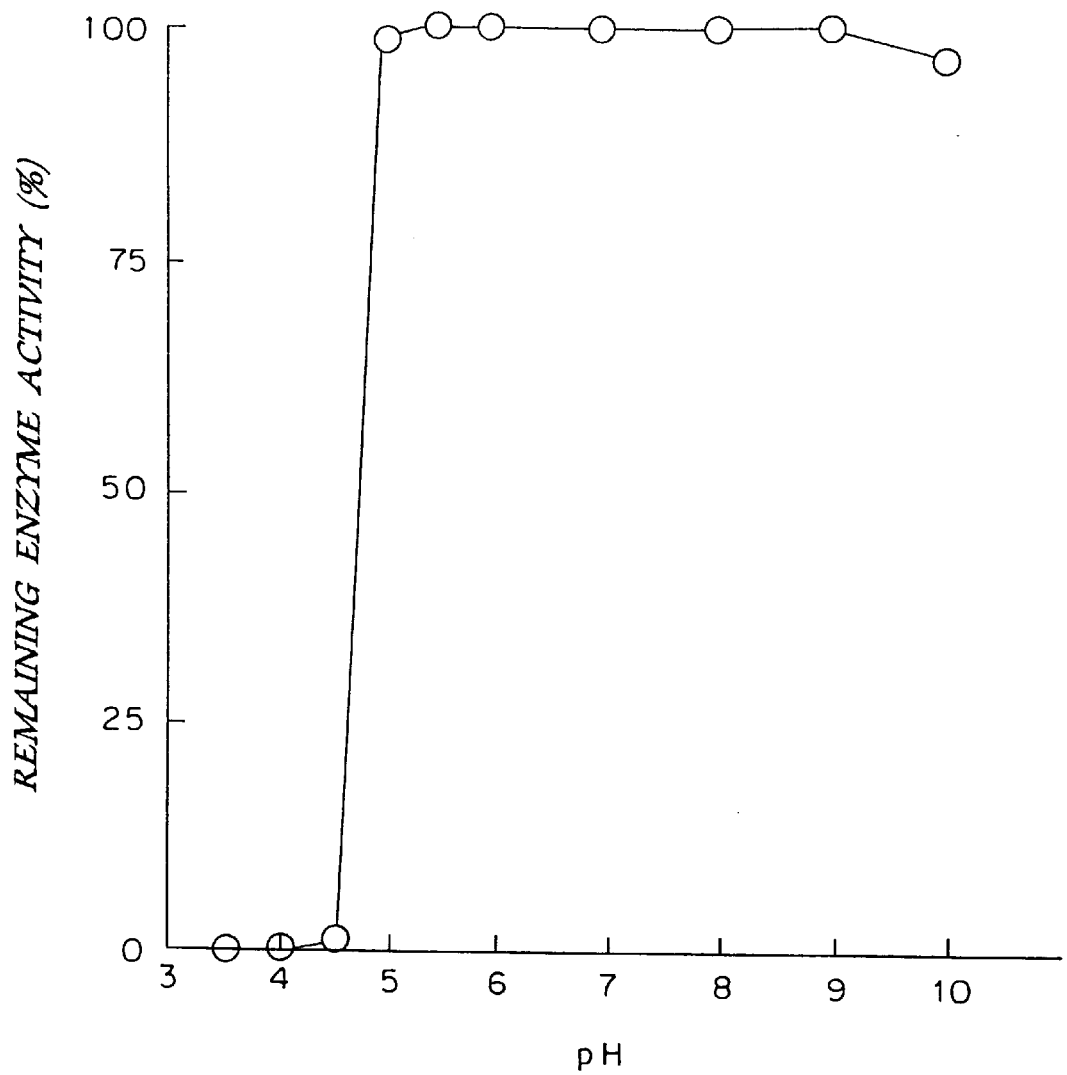
FIG. 4 illustrates the pH stability of a non-reducing saccharide-forming enzyme from Rhizobium M-11.

Effects of temperature and pH on enzymatic activity were tested in accordance with the aforementioned assay method. The results were as shown in FIGS. 1 (effect of temperature) and 2 (effect of pH) respectively. The optimum temperature was found around 40° C. when incubated at pH 7.0 for 60 minutes, while the optimum pH was about 7.0 when incubated at 40° C. for 60 minutes. Thermal stability of the enzyme was determined by incubating it in 50 mM phosphate buffer, pH 7.0 at different temperatures for 60 minutes, followed by cooling the solution in water bath and assaying the residual enzymatic activity. While the pH stability was determined by incubating the enzyme in 50 mM phosphate buffer at different pHs and 25° C. for 16 hours, adjusting the buffers to pH 7.0 and assaying the residual activities. The results were shown in FIGS. 3 (thermal stability) and 4 (pH stability) respectively. The enzyme was stable at a temperature up to 40° C. and at a pH in the range of about 6–9.

Experiment A-4

Preparation of non-reducing saccharide

Aqueous solutions containing 20 w/v % of either glucose, maltose, maltotriose, maltotetraose, maltopentaose, maltohexaose or maltoheptaose as substrate were admixed with 2 units/g substrate solid of the purified enzyme preparation obtained in Experiment A-2 and reacted at 40° C. and pH 7.0 for 48 hours and the resultant solutions were deionized and analyzed for reaction products on high-performance liquid chromatography using "WAKO BEADS®WB-T-330" (a column of Wako Pure Chemical Industries, Ltd., Osaka, Japan). The high-performance liquid chromatography was carried out at ambient temperature, and water as eluent was applied to the column at a flow rate of 0.5 ml/minute while monitoring eluate with "RI-8012", a differential refractometer (a product of Tosoh Corporation, Tokyo, Japan). The results were as shown in Table 2.

As evident from the results in Table 2, the reaction products consisted of residual substrates and newly formed saccharides PI, PII, PIII, PIV and PV and no other saccharides were substantially detected.

TABLE 2

| Substrate | Reaction product | Elution Time on HPLC (minutes) | Composition (%) |
| --- | --- | --- | --- |
| Glucose | Glucose | 33.4 | 100.0 |
| Maltose | Maltose | 28.5 | 100.0 |
| Maltotriose | PI | 23.3 | 35.0 |
|  | Maltotriose | 25.9 | 65.0 |
| Maltotetraose | PII | 21.6 | 85.6 |
|  | Maltotetraose | 24.1 | 14.4 |

TABLE 2-continued

| Substrate | Reaction product | Elution Time on HPLC (minutes) | Composition (%) |
| --- | --- | --- | --- |
| Maltopentaose | PIII | 19.7 | 92.7 |
|  | Maltopentaose | 22.6 | 7.3 |
| Maltohexaose | PIV | 18.7 | 93.5 |
|  | Maltohexaose | 21.4 | 6.5 |
| Maltoheptaose | PV | 17.8 | 93.4 |
|  | Maltoheptaose | 21.0 | 6.6 |

Note: PI, PII, PIII, PIV and PV in the Table designate the newly formed products from respective substrates, i.e. maltotriose, maltotetarose, maltopentaose, maltohexaose and maltoheptaose.

The yields for PI having a glucose polymerization degree of 3 was relatively low, however, that for PII, PIII, PIV and PV, which had a glucose polymerization degree of 4 or higher, were high, i.e. 85% or higher. It was revealed that no saccharide was formed from glucose and maltose.

For purifying these newly formed saccharides, the reaction products were decolored, deionized, concentrated and subjected to column fractionation using a strongly-acidic cation exchanger in alkali metal form ("XT-1016", Na+ form, 4% cross-linking degree, a product of Tokyo Organic Chemical Industries, Ltd., Tokyo, Japan). More particularly, the cation exchanger was packed in 3 jacketed stainless steel columns, inner diameter of 2.0 cm, length of 1 cm each, cascaded in series, which were then loaded with either reaction product in an amount of 5 v/v % against the volume of the cation exchanger and then applied with 55° C. water at SV (space velocity) 0.13 for fractionation, and followed by collecting the fractions containing 97% or more newly formed saccharides. The obtained fractions were separately lyophilized into high-purity saccharide preparations. The yields against particular material substrates were about 9% for PI, about 65% for PII, about 82% for PIII, about 80% for PIV and about 77% for PV, and the final purities were 97.5% for PI, 98.6% for PII, 99.5% for PIII, 98.4% for PIV and 98.4% for PV.

These high-purity saccharide preparations were tested for reducing power with the Somogyi-Nelson method and their reducing powers were represented by DE (dextrose equivalent). The results were given in Table 3.

TABLE 3

| Saccharide preparation | Purity (%) | DE |
| --- | --- | --- |
| PI | 97.5 | 0.83 |
| PII | 98.6 | 0.35 |
| PIII | 99.5 | 0.10 |
| PIV | 98.4 | 0.27 |
| PV | 98.4 | 0.23 |

As evident from the results in Table 3, all the preparations exhibited only a slight reducing power. It was suggested that the reducing powers would be due to a trace amount of reducing maltooligosaccharides from the substrates which had remained in the preparations, and that all the newly formed saccharides were substantially free from reducing power.

Experiment A-5

Enzymatic degradation using glucoamylase

Fifty milligrams of either non-reducing saccharide preparation PI, PII, PIII, PIV or PV obtained in Experiment A-4 was dissolved in 1 ml of 50 mM acetate buffer (pH 4.5) and the resultant solutions were admixed with 1 unit of glucoamylase (a product of Seikagaku Corporation, Tokyo, Japan), incubated at 40° C. for 6 hours for enzymatic degradation and analyzed for degradation products on high-performance liquid chromatography. As the results, only glucose and trehalose were detected in all the hydrolyzed products. The contents and molar ratios of glucose and trehalose were as shown in Table 4.

TABLE 4

| Saccharide preparation | Glucose (%) | Trehalose (%) | Molar ratio (glucose/trehalose) |
| --- | --- | --- | --- |
| PI  | 36.2 | 63.8 | 1.07 |
| PII | 52.0 | 48.0 | 2.06 |
| PIII | 61.4 | 38.6 | 3.02 |
| PIV | 68.3 | 31.7 | 4.09 |
| PV  | 72.9 | 27.1 | 5.11 |

As evident from the results in Table 4, it was revealed that PI was degraded by glucoamylase into 1 glucose molecule and 1 trehalose molecule; PII, into 2 glucose molecules and 1 trehalose molecule; PIII, into 3 glucose molecules and 1 trehalose molecule; PIV, into 4 glucose molecules and 1 trehalose molecule; and PV, into 5 glucose molecules and 1 trehalose molecule.

Considering the reaction characteristics of glucoamylase, these non-reducing saccharide preparations would have a structure where one or more glucose molecules are bound to trehalose molecule via the α-1,4 or α-1,6 linkage: In particular, PI is a non-reducing saccharide with a glucose polymerization degree of 3 where 1 glucose molecule is bound to 1 trehalose molecule; PII, a non-reducing saccharide with a glucose polymerization degree of 4 where 2 glucose molecules are bound to 1 trehalose molecule; PIII, a non-reducing saccharide with a glucose polymerization degree of 5 where 3 glucose molecules are bound to 1 trehalose molecule; PIV, a non-reducing saccharide with a glucose polymerization degree of 6 where 4 glucose molecules are bound to 1 trehalose molecule; and PV, a non-reducing saccharide with a glucose polymerization degree of 7 where 5 glucose molecules are bound to 1 trehalose molecule. It was revealed that after exposing PI, PII, PIII, PIV and PV to β-amylase, PI and PII were not hydrolyzed but PIII was hydrolyzed into 1 maltose molecule and one PI molecule; PIV, into 1 maltose molecule and 1 PII molecule; and PV, into 2 maltose molecules and 1 PI molecule.

The above results suggest that the reaction by the non-reducing saccharide-forming enzyme according to this invention would be an intramolecular conversion reaction which does not accompany neither degradation nor polymerization of substrates, in other words, it does not change their glucose polymerization degrees. Thus PI, PII, PIII, PIV and PV produced by the enzyme would be α-glucosyl trehalose (as represented by Gn-T where G and T represent glucose residue and α, α-trehalose respectively, while n is an integer of 1 or more), i.e. α-glucosyl trehalose (or α-maltosyl glucoside), α-maltosyl trehalose (or α-maltotriosyl glucoside), α-maltotriosyl trehalose (or α-maltotetraosyl glucoside), α-maltotetraosyl trehalose (or α-maltopentaosyl glucoside) and α-maltopentaosyl trehalose (or α-maltohexaosyl glucoside) respectively.

Experiment A-6
Preparation of trehalose and non-reducing saccharide having trehalose structure as an end unit Forty parts by weight of a partial starch hydrolysate ("PINE-DEX #4", a product of Matsutani Chemical Ind., Co., Ltd., Kyoto, Japan) was dissolved in 60 parts by weight of water by heating and the resultant solution was heated to 45° C. and adjusted pH 6.5, admixed with 1 unit/g reducing partial starch hydrolysate of a non-reducing saccharide-forming enzyme prepared by the method in Experiment A-2 and reacted for 96 hours to form non-reducing saccharides having a trehalose structure as an end unit, followed by heating at 100° C. for 10 minutes to inactivate the enzyme. The reaction mixture was then diluted up to about 20%, admixed with 10 units/g partial starch hydrolysate of "GLUCOZYME", a glucoamylase or specimen commercialized by Nagase Biochemicals Ltd., Kyoto, Japan, reacted for 40 hours and heated to inactivate the enzyme. The resultant solution was decolored with activated charcoal, deionized with ion-exchanger and concentrated to about 60% solution in usual manner. The obtained saccharide solution contained 29.5% trehalose. This concentrate was then charged to a stainless steel column prepacked with a strongly-acidic cation exchanger ("CG6000", $Na^+$ form, a product of Japan Organo, Co., Ltd., Tokyo, Japan) at 60° C. and SV 0.4, and fractions which were rich in trehalose. The fractions contained about 90% trehalose. The fractions were collected and the solution was concentrated to about 75%, fed in a crystallizer, admixed with about 2% crystalline trehalose hydrate as a seed crystal and gradually cooled to obtain a massecuit which had a crystallinity of about 45%. The massecuit thus obtained was then sprayed from a nozzle equipped on the upper part of a drying tower at a pressure of 150 kg/cm$^2$. At the same time, 85° C. air was sent from the upper part of the drying tower towards its bottom and the resultant powder, which had been accumulated on a wire netting of a conveyer provided at the bottom of the drying tower, was gradually conveyed out from the drying tower while sending thereto 45° C. air under the wire netting. Thereafter the crystalline powder was fed to an aging tower and aged in a stream of hot air for 10 hours to complete its crystallization and dehydration, thus obtaining crystalline trehalose hydrate powder.

Experiment B-1
Preparation of crystalline maltotetraosyl glucoside

Five parts by weight of 98% maltopentaose (a product of Hayashibara Biochemical Laboratories, Inc., Okayama, Japan) were dissolved in 100 parts by weight of water on heating and the resultant solution was heated to 40° C. and adjusted to pH 7.0, admixed with a non-reducing saccharide-forming enzyme prepared by the method in Experiment A-2 in an amount of 2 units/g maltopentaose, and then reacted for 48 hours and followed by heating at 100° C. for 20 minutes to inactivate the enzyme. The solution was allowed to stand in 4° C. cool room over night to form a precipitate. The suspension thus precipitated was adjusted to 0.1N by adding sodium hydroxide, and heated at 100° C. for 2 hours to decompose reducing saccharides. The resultant solution was decolored with activated charcoal and purified with ion-exchanger ($H^+$ and $OH^-$ form) to obtain 97.5% maltotetraosyl glucoside fraction. The fractions were pooled and the solution was concentrated to give a concentration of 50%, allocated to a glass beaker and allowed to stand at 25° C. for 1 hour to form a crystal on the inner wall of the beaker. The resultant crystal was collected by a centrifuge and washed by spraying thereto a small amount of water to obtain 99.5% hydrous crystalline maltotetraosyl glucoside product. The product was dried under a reduced pressure at 100° C. over night to obtain an anhydrous crystalline product.

These crystalline products were determined for their physicochemical properties and the results were as follows:
   (1) Elemental analysis (as anhydride)
      Hydrous crystal C=43.13%, H=6.37%
      Anhydrous crystal C=43.20%, H=6.35%
      Theoretical value C=43.48%, H=6.32%

(2) Mass spectrum analysis (as anhydride)
MW=828 (for molecular formula: $C_{30}H_{52}O_{26}$)

(3) Water content

Measured by the Karl Fischer's method
Hydrous crystal 4.2% (molar ratio of maltotetraosyl glucoside to water=1:2)
Anhydrous crystal 0.2%

(4) Melting point

Allocated 1 mg of hydrous or anhydrous crystal of maltotetraosyl glucoside respectively to a specific aluminum vessel, and measured by a differential scanning calorimeter DSC-8230 (commercialized by RIGAKU International Corporation, Tokyo, Japan). Hydrous crystal exhibited two endothermic peaks at 170 to 172° C. and 230 to 233° C., and anhydrous crystal exhibited an endothermic peak at 230 to 233° C. It is considered that the endothermic peak at 230 to 233° C. as observed in hydrous crystal was caused by converting hydrous crystal into anhydrous crystal during on the increase of temperature rate, therefore, the melting point of hydrous crystal or anhydrous crystal is considered to be 170 to 172° C. or 230 to 233° C. respectively.

(5) Specific rotatory power (as anhydride)

Both hydrous and anhydrous crystals had the following specific rotatory power.

$[\alpha]_D^{20}$ +208.8° (c=1.0, $H_2O$)

(6) Ultraviolet absorption spectrum

Both hydrous and anhydrous crystals exhibited no characteristic absorption spectra, when analyzed in their aqueous solutions.

(7) Infrared absorption spectrum

Figure 5:
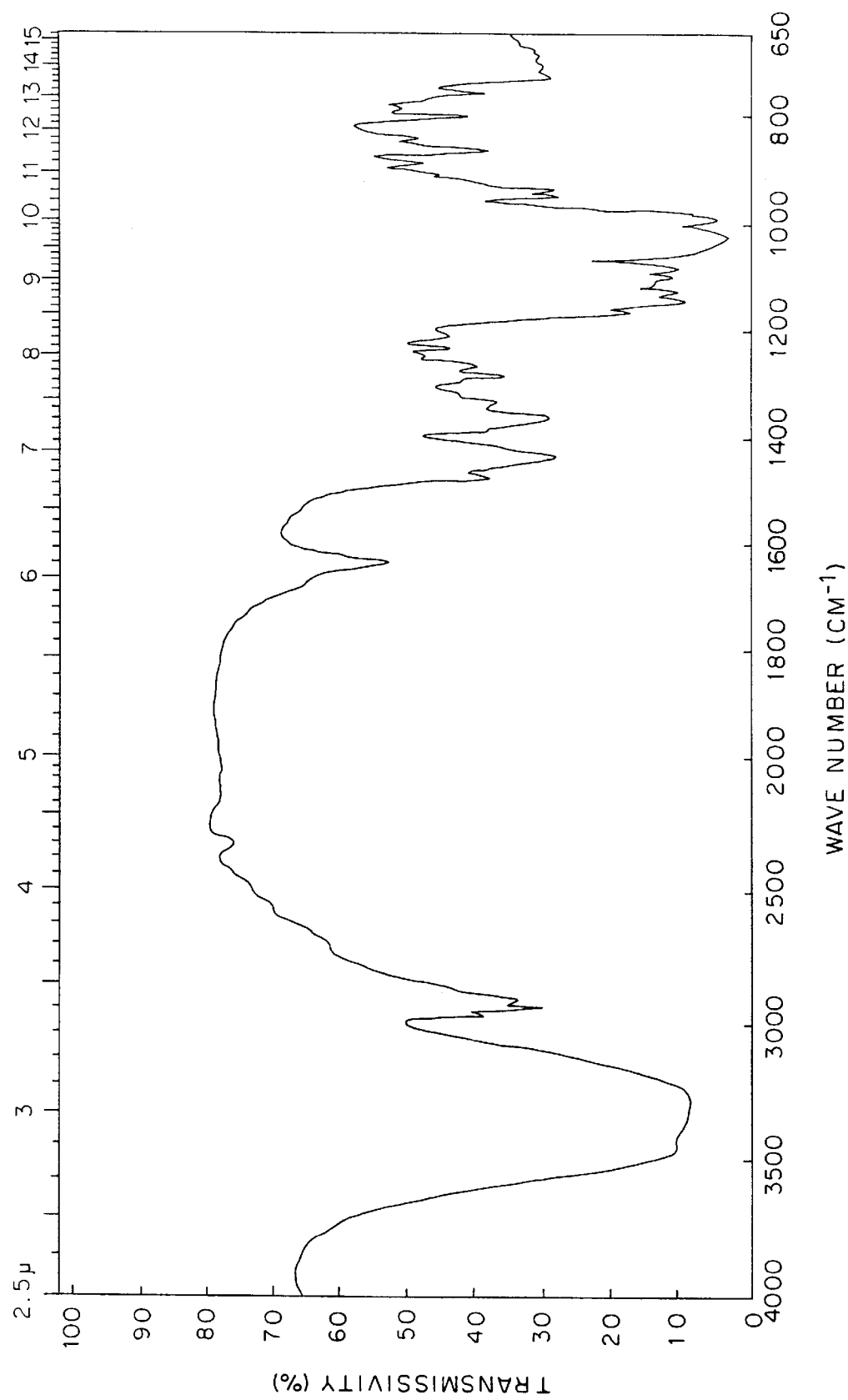
FIG. 5 illustrates the infrared absorption spectrum of hydrous crystalline maltotetraosyl glucoside.
Figure 6:
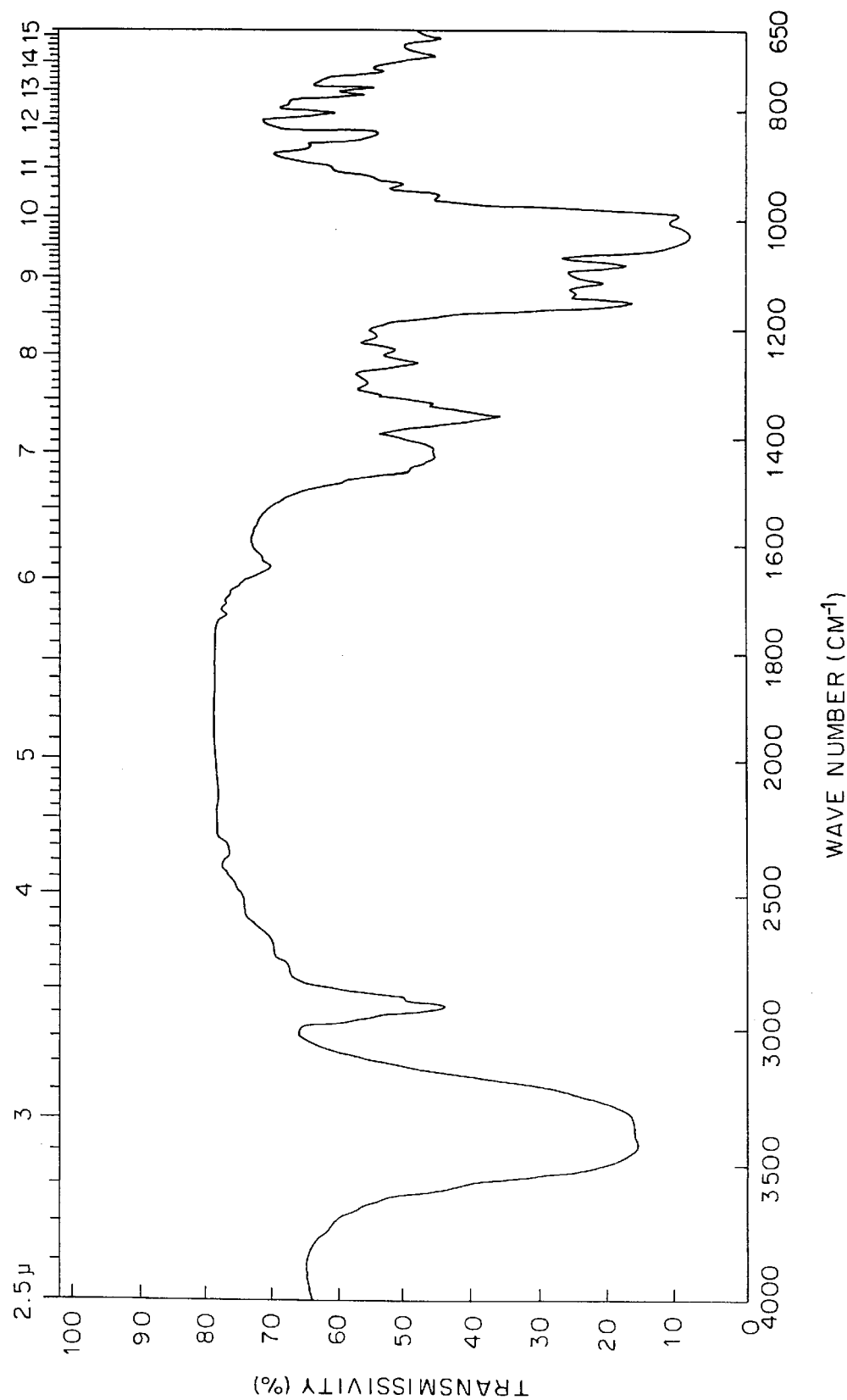
FIG. 6 illustrates the infrared absorption spectrum of anhydrous crystalline maltotetraosyl glucoside.

Two milligrams of powdered hydrous or anhydrous crystal and 200 mg of dried KBr were mixed and prepared into a transparent tablet which was then analyzed for infrared absorption spectrum. The results of hydrous and anhydrous crystal were as shown in FIGS. 5 and 6.

(8) Solubility (as anhydride)

Up to about 1 g each hydrous or anhydrous crystal was soluble in 100 ml of 25° C. water.

(9) Sweetness

A saturated solution of crystalline maltotetraosyl glucoside exhibited a slightly tastable low sweetness.

(10) Coloring reaction

The hydrous and anhydrous crystals colored into green upon the anthrone-sulfuric acid reaction but were negative to both the Fehling's reaction and iodine reaction.

(11) Structure (as anhydride)

(a) Upon hydrolysis by 1N sulfuric acid, the crystals formed D-glucose only.

(b) When exposed to glucoamylase, the crystals each formed three moles of glucose and one mole of trehalose.

Figure 7:
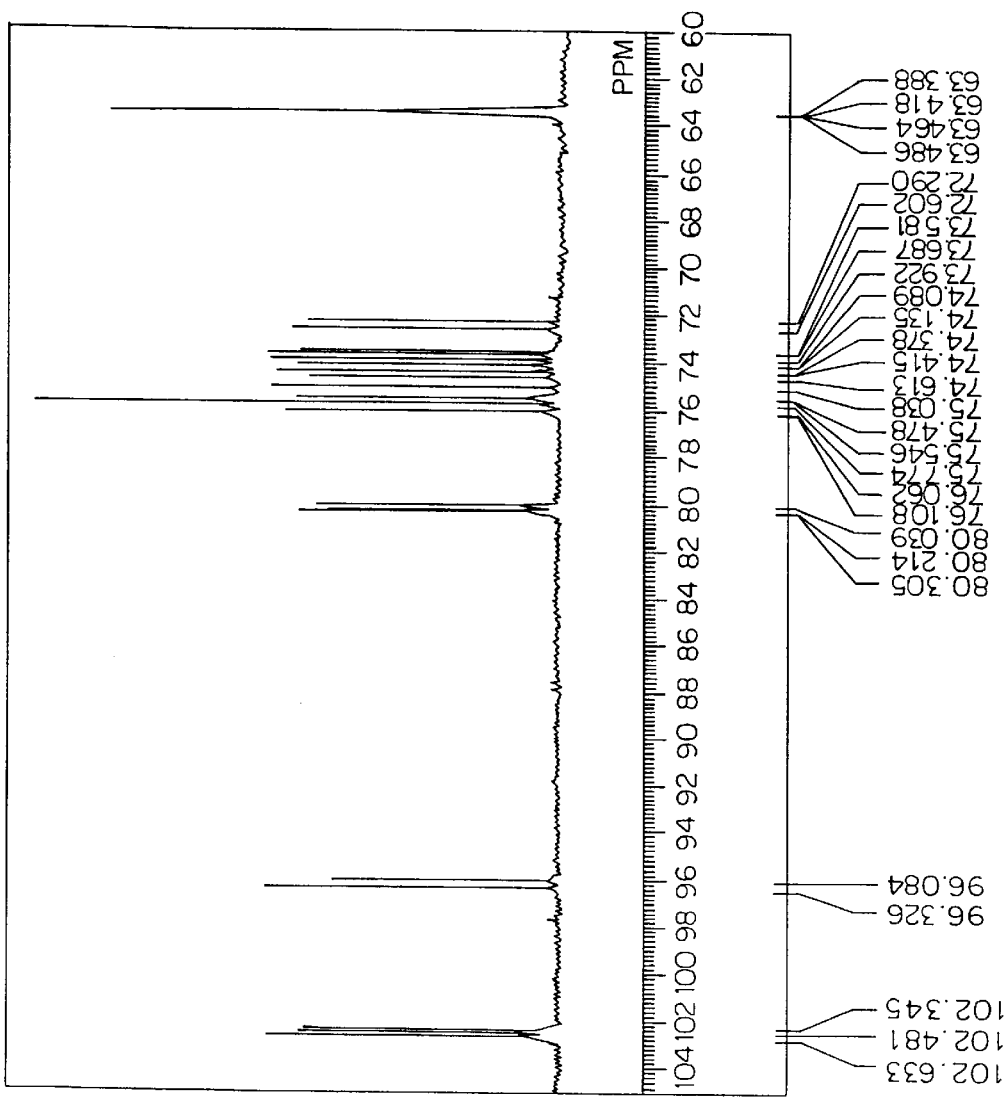
FIG. 7 illustrates the results of carbon nuclear resonance analysis of maltotetraosyl glucoside.

(c) The result on carbon nuclear resonance analysis ($^{13}$C-NMR) was as shown in FIG. 7. All the carbon atoms of the crystals were assigned to the chemical shifts of α-D-glucopyranose, α, α-trehalose and maltotetraose as standard substances reported by Klaus Bock et al., in *Advances in Carbohydrate Chemistry and Biochemistry*, Vol.42, pp.193–225 (1984) and it was suggested that the crystals had a structure represented by O-α-D-glucopyranosyl-(1→4)-O-α-D-glucopyranosyl-(1→4)-O-α-D-glucopyranosyl-(1→4)-α-D-glucopyranosyl α-D-glucopyranoside, that is maltotetraosyl glucoside structure.

(12) Powder X-ray diffraction

Figure 8:
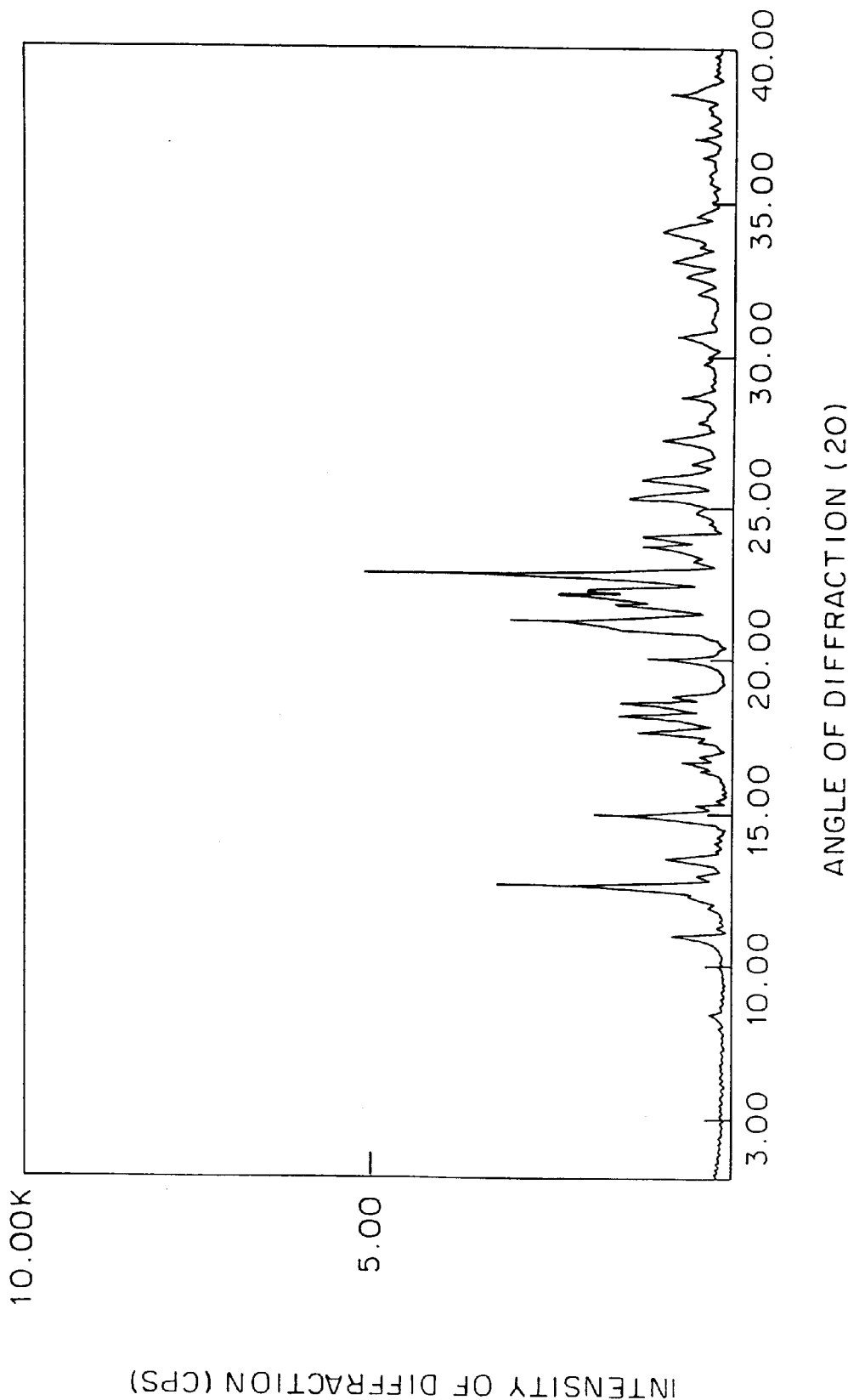
FIG. 8 illustrates the powder X-ray diffraction figure of hydrous crystalline maltotetraosyl glucoside.

Crystalline maltotetraosyl glucoside was determined for powder x-ray diffraction figure using CuKα-ray in accordance with the method reported by F. H. Stodola et at. in *Journal of the American Chemical Society*, Vol.78, pp.2,514–2,518 (1956). The result of hydrous crystal or anhydrous crystal was as shown in FIG. 8 or FIG. 9 respectively. As evident from the results in FIGS. 8 and 9, hydrous crystal gave predominant, main or major diffraction angles (2θ) of 12.6°, 21.3°, 22.1° and 22.8°, while anhydrous crystal gave predominant, main or major diffraction angles of 12.7°, 13.7°, 18.8° and 23.2° on powder x-ray diffraction analysis.

Based on the above results, the crystals of the present invention can be acknowledged as the crystals of maltotetraosyl glucoside which have been unknown.

Experiment B-2

Acute toxicity

Hydrous and anhydrous crystalline maltotetraosyl glucosides prepared by the method in Experiment B-1 were tested for acute toxicity in mice upon oral administration. As the results, these crystalline maltotetraosyl glucosides were found to be low in toxicity and no mouse was died even administered with their maximum administrable doses. These suggest that their $LD_{50}$ would be briefly 50 g/kg or higher.

The following Example A and Example B will illustrate the production of crystalline maltotetraosyl glucosides and uses of the same respectively.

EXAMPLE A-1

Fifty parts by weight of 98% maltopentaose, a product commercialized by Hayashibara Biochemical Laboratories, Inc., Okayama, Japan, was dissolved in 200 parts by weight of water while heating and the resultant solution was heated to 40° C. and adjusted to pH 7.0, admixed with a non-reducing saccharide-forming enzyme prepared by the method in Experiment A-2 in an amount of 5 units/g maltopentaose, reacted for 24 hours and followed by heating at 100° C. for 20 minutes to inactivate the enzyme. The resultant solution contained about 90% maltotetraosyl glucoside, and the remains are maltopentaose. The solution was adjusted to 0.1N by adding sodium hydroxide, and heated at 100° C. for 2 hours to decompose reducing saccharides. The solution was decolored with activated carbon and desalted with ion-exchange resins ($H^+$ and $OH^-$ form) to obtain 98% maltotetraosyl glucoside fraction. The fractions were pooled and the solution was concentrated to give a concentration of 60%, placed in a crystallizer and admixed with a crystalline maltotetraosyl glucoside in an amount of 2% as a seed crystal, and the resultant mixture is cooled gradually while stirring for crystallization to form a massecuit. The massecuit thus obtained was separated from molasses to obtain 99.9% hydrous crystalline maltotetraosyl glucoside in the yield against starting material of about 50%. The crystalline maltotetraosyl glucoside thus obtained exhibited no hygroscopicity when allowed to stand in a room.

The crystalline maltotetraosyl glucoside of this invention is favorably usable as a seed crystal, in addition, as reagents, substrates for assaying amylase in serum and chemical raw materials, and furthermore favorably useful in a variety of compositions including foods, beverages, cosmetics, pharmaceuticals and shaped bodies.

EXAMPLE A-2

About 20% potato starch containing 0.1% calcium carbonate was adjusted to pH 6.0, and then admixed with "TERMAMYL® 60L", α-amylase commercialized by Novo Nordisk Bioindustry, Copenhagen, Denmark, in an amount of 0.3% with respect to starch solid, liquefied at 95–100° C. and heated to inactivate the enzyme, thus a liquefied starch solution with DE 19.5 was obtained. The resultant solution was heated to 40° C. and adjusted to pH 6.2, admixed with a non-reducing saccharide-forming enzyme prepared by the method in Experiment A-2 in an amount of 3 units/g starch together with isoamylase, commercialized by Hayashibara Biochemical Laboratories, Inc., Okayama, Japan, in an amount of 1000 units, and reacted for 72 hours. The mixed solution was heated at 95° C. for 10 minutes to inactivate the enzymes. The solution contained about 30% maltotetraosyl glucoside, and decolored with activated charcoal, desalted by ion-exchange resins ($H^+$ and $OH^-$ form) and concentrated to give a concentration of 40%. This concentrate was then charged to a jacketed stainless steel column (cascaded 4 columns, 5.4 cm×4 m) prepacked with a strongly-acidic cation exchanger ("XT-1016", $Na^+$ form, a product of Japan Organo, Co., Tokyo, Japan) at 60° C. and SV 0.4, and eluted with 60° C. water to obtain fractions which were rich in maltotetraosyl glucoside. The fractions contained about 92% maltotetraosyl glucoside, and the fractions were pooled and the solution was decolored with activated charcoal, desalted with ion-exchange resin ($H^+$ and $OH^-$ form) and concentrated in usual manner to give about 80% concentration, d.s.b., and placed in a crystallizer and admixed with a crystalline maltotetraosyl glucoside in the amount of 1% as a seed crystal, and the resultant mixture is cooled gradually while stirring for crystallization to form a massecuite. The massecuite thus obtained was allocated to a vessel to form a block. The block was allowed to stand at about 25° C. for 2 days and followed by aging, pulverized by a cutting-type pulverizer, and followed by fluidized-drying and scaling to obtain a hydrous crystalline maltotetraosyl glucoside powder in the yield of about 30%.

The product thus obtained exhibits substantially no hygroscopicity and is readily handleable, and it is favorably useful in a variety of compositions including foods, beverages, cosmetics, pharmaceuticals and shaped bodies as a sweetener, taste improver, quality improver, stabilizer and vehicle.

EXAMPLE A-3

"PINE-DEX #4", a partial starch hydrolysate commercialized by Matsutani Chemical Ind., Co., Ltd., Kyoto, Japan, was adjusted to 20% concentration, 45° C. and pH 5.5, and admixed with 500 units/g partial starch hydrolysate of isoamylase, commercialized by Hayashibara Biochemical Laboratories, Inc., Okayama, Japan, and reacted for 24 hours to decompose the α-1,6 linkages of starch. The solution thus reacted was heated at 100° C. and allowed to stand for 10 minutes, and then cooled to 40° C. and adjusted to pH 6.5. The resultant solution was admixed with 5 units/g solid of non-reducing saccharide-forming enzyme prepared by the method in Experiment A-2 and "TERMAMYL® 60L", α-amylase commercialized by Novo Nordisk Bioindustry, Copenhagen, Denmark, in an amount of 0.3% with respect to starch solid, and reacted for 48 hours. The solution was heated to inactivate the enzymes and cooled. The solution contained about 32% maltotetraosyl glucoside, and was purified, concentrated and applied to a chromatography using a strongly-acidic cation exchange resin similarly to Example A-1 to obtain the fractions which were rich in maltotetraosyl glucoside. The fractions contained about 81% maltotetraosyl glucoside. The fractions were pooled and the solution was decolored with activated charcoal, desalted with ion-exchange resin ($H^+$ and $OH^-$ form) and concentrated in usual manner to give about 70% concentration, and placed in a crystallizer and admixed with a crystalline maltotetraosyl glucoside in an amount of 2% as a seed crystal, and the resultant mixture is cooled gradually while stirring for crystallization to form a massecuite with about 70% crystallinity. The massecuit was then sprayed from a nozzle equipped on the upper part of a drying tower at a pressure of 150 kg/cm². At the same time, 85° C. air was sent from the upper part of the drying tower towards its bottom and the resultant powder, which had been accumulated on a wire netting of a conveyer provided at the bottom of the drying tower, was gradually conveyed out from the drying tower while sending thereto 45° C. air under the wire netting. Thereafter the crystalline powder was fed to an aging tower and aged in a stream of hot air for 24 hours to complete its crystallization and dehydration, thus a powder containing crystalline maltotetraosyl glucoside was obtained in the yield against the starting material of about 25%.

The product thus obtained, which exhibits substantially no hygroscopicity and is readily handleable, is favorably useful in a variety of compositions including foods, beverages, cosmetics, pharmaceuticals and shaped bodies as a sweetener, taste improver, quality improver, stabilizer and vehicle.

EXAMPLE A-4

The hydrous crystalline maltotetraosyl glucoside which had been prepared by the same methods as in Example A-1 was dried at 100° C. under reduced pressure over night to obtain an anhydrous crystalline maltotetraosyl glucoside having about 0.2% water content.

The product, when allowed to stand in a room, exhibited hygroscopicity and was converted into hydrous crystalline maltotetraosyl glucoside having about 4% water content for stabilization. The anhydrous crystalline maltotetraosyl glucoside can be favorably used as hygroscopic agent, dehydrating agent and chemical raw material, and further utilizable in a variety of compositions including foods, beverages, cosmetics, pharmaceuticals and shaped bodies, similar to hydrous crystalline maltotetraosyl glucoside in Example A-1.

EXAMPLE A-5

One part by weight of trehalose and one part by weight of "PINE-DEX #4", a partial starch hydrolysate commercialized by Matsutani Chemical Ind., Co., Ltd., Kyoto, Japan, were dissolved in 3 parts by weight of water while heating, and the resultant solution was heated to 65° C. and adjusted to pH 6.0, admixed with 10 units/g partial starch hydrolysate of a cyclomaltodextrin glucanotransferase derived from *Bacillus stearothermophilus* commercialized by Hayashibara Biochemical Laboratories, Inc., Okayama, Japan, reacted for 24 hours and heated to inactivate the enzyme. Thereafter the solution was adjusted to 55° C., admixed with 25 units/g partial starch hydrolysate of pullulanase commercialized by Hayashibara Biochemical Laboratories, Inc., Okayama, Japan, and with 5 units/g partial starch hydrolysate of "TERMAMYL® 60L", α-amylase commercialized by Novo Nordisk Bioindustry, Copenhagen, Denmark, respectively, and reacted for 24 hours and heated to inactivate the enzymes. The solution contained about 15% maltotetraosyl glucoside. The solution thus obtained was purified and applied to a chromatography using a strongly-acidic cation exchange resin in the same way as that in Example A-2 to obtain the fractions which were rich in maltotetraosyl glucoside. The fractions were pooled and the solution was decolored, desalted, concentrated, crystallized and allocated into a vessel to form a block. The block was pulverized, drying and classifying to obtain a powder containing a hydrous crystalline maltotetraosyl glucoside in the yield against starting material of about 10%.

The product thus obtained exhibits substantially no hygroscopicity and is readily handleable, and it is favorably useful in a variety of compositions including foods, beverages, cosmetics, pharmaceuticals and shaped bodies as a sweetener, taste improver, quality improver, stabilizer and vehicle.

EXAMPLE B-1

Sweetener

Half part by weight of a powder containing hydrous crystalline maltotetraosyl glucoside obtained by the method in Example A-2, 1.5 part by weight of "SUNMALT®", a crystalline maltose commercialized by Hayashibara Shoji, Inc., Okayama, Japan, and 0.1 parts by weight of "α G SWEET", α-glycosyl stevioside commercialized by Toyo Sugar Refining Co., Ltd., Tokyo, Japan, were mixed to homogeneity and the mixture was fed to granulator to obtain a granular sweetener.

The sweetener has a superior taste quality and about twofold stronger sweetening power and the calorie in terms of sweetening power is about one half of that of sucrose. The sweetener is suitable as a low-calorie sweetener to sweeten low-calorie foods and beverages for those having obesity or diabetes whose calorie intakes are restricted, and furthermore the sweetener is also suitable to sweeten foods and beverages which are directed to suppress dental caries because it is less in acid and insoluble glucan production by cariogenic microorganisms.

EXAMPLE B-2

Lactic acid beverage

Ten parts by weight of defatted milk was pasteurized at 80° C. for 20 minutes, cooled to 40° C., admixed with 0.3 parts by weight of starter and fermented at 37° C. for 10 hours. The resultant was homogenized, admixed with 0.4 parts by weight of a hydrous crystalline maltotetraosyl glucoside obtained by the method in Example A-3, 1.6 parts by weight of "TETRUP®", maltotetraose syrup commercialized by Hayashibara Shoji, Inc., Okayama, Japan, 1 part by weight of sucrose and 3 parts by weight of isomerized sugar, and the mixture was pasteurized by keeping it at 70° C. The mixture was cooled, admixed with an appropriate amount of flavoring agent and bottled to obtain lactic acid beverage.

The product is a high-quality lactic acid beverage having flavor and sweetness which are well harmonized with sour taste.

EXAMPLE B-3

Powdered juice

Thirty three parts by weight of spray-dried orange juice was admixed to homogeneity with 5 parts by weight of a hydrous crystalline maltotetraosyl glucoside powder obtained by the method in Example A-5, 35 parts by weight of crystalline maltose, 20 parts by weight of sucrose, 0.65 parts by weight of citric anhydride, 0.1 part by weight of malic acid, 0.1 part by weight of L-ascorbic acid, 0.1 part by weight of sodium citrate, 0.5 parts by weight of pullulan and an appropriate amount of powdered flavoring agent, pulverized into a fine powder, fed to fluidized-bed granulator and granulated at ventilation temperature of 40° C. for 30 minutes while spraying thereto with starch syrup as a binder, and divided into a prescribed amount and packaged to obtain powdered juice.

The product is a powdered juice which has an about 30% natural fruit juice, and is free of undesirable taste and smell, hygroscopicity and solidification, and very stable over an extended storage period.

EXAMPLE B-4

Chocolate

Forty parts by weight of cacao paste, 10 parts by weight of cacao butter, 5 parts by weight of a hydrous crystalline maltotetraosyl glucoside obtained by the method in Example A-1, 10 parts by weight of crystalline maltose and 35 parts by weight of sucrose were mixed, and the resultant mixture was fed to a refiner to reduce particle size, fed to a conche and kneaded at 50° C. for 2 days. While such kneading, the mixture was admixed with 0.5 parts by weight of lecithin, sufficiently mixed and dispersed. Thereafter the mixture was kept at 31° C. with thermo-controller, poured in molds immediately before solidification of the butter, deaerated with vibrator and passed through 10° C. cooling tunnel over 20 minutes to complete solidification. The contents in the molds were then taken out and packaged to obtain chocolate.

The product, having no hygroscopicity, superior color, gloss and texture, has a satisfiable inner texture and smoothly melts in the mouth to exhibit a gentle sweetness and mild flavor.

EXAMPLE B-5

Chewing gum

Three parts by weight of gum base was softened by heating, admixed with 3 parts by weight of "MABIT®", a crystalline maltitol commercialized by Hayashibara Shoji, Inc., Okayama, Japan, 3 parts by weight of sucrose and 1 part by weight of a powder containing hydrous crystalline maltotetraosyl glucoside obtained by the method in Example A-2, admixed with appropriate amounts of flavoring and coloring agents, kneaded with roller, shaped and packaged in usual manner to obtain chewing gum.

The product is a chewing gum having a superior texture, flavor and taste.

EXAMPLE B-6

"Uiro-no-moto (instant "uiro")

Ninety parts by weight of rice powder was admixed to homogeneity with 20 parts by weight of corn starch, 10 parts by weight of a powder containing crystalline maltotetraosyl glucoside obtained by the method in Example A-3, 60 parts by weight of maltotetraose powder, 50 parts by weight of sucrose and 4 parts by weight of pullulan to homogeneity to obtain "uiro-no-moto". The "uiro-no-moto" was kneaded with appropriate amounts of "maccha" (a green tea powder)" and water and the resultant mixture was divided in vessels and steamed for 60 minutes to obtain "maccha-uiro".

The product has a smooth gloss, good palatability and delicious taste, and also has a long shelf life because retrogradation of starch is effectively suppressed.

EXAMPLE B-7

Solidified feeding for liquid foods

A composition consisting of 100 parts by weight of anhydrous crystalline maltotetraosyl glucoside obtained by the method in Example A-4, 100 parts by weight of crystalline maltose, 350 parts by weight of maltotetraose powder, 270 parts by weight of dried yolk, 209 parts by weight of defatted milk, 4.4 parts by weight of sodium chloride, 1.85 parts by weight of potassium chloride, 4 parts by weight of magnesium sulfate, 0.01 part by weight of thiamine, 0.1 part by weight of sodium ascorbate, 0.6 parts by weight of vitamin E acetate and 0.04 parts by weight of nicotine amide was prepared, and the composition was divided into 25 g aliquot in small laminated aluminum packs which were then heat-sealed.

One pack of the product is dissolved in about 150–300 ml water and the resultant solution is usable as a liquid feeding parenterally administerable to the nasal cavity, stomach or intestine.

EXAMPLE B-8

Traumatic ointment

Twenty parts by weight of hydrous crystalline maltotetraosyl glucoside obtained by the method in Example A-1, 280 parts by weight of crystalline maltose and 200 parts by weight of maltotetraose powder were admixed with 50 parts by weight of methanol containing 3 parts by weight of iodine, and the resultant was mixed with 200 parts by weight of 10% pullulan to obtain a traumatic ointment which has an appropriate extensity and adhesiveness.

The product allows to shorten a therapeutic period and cure traumas without a scar.

EXAMPLE B-9

Sugar coated tablet

A crude tablet having 150 mg weight was sugar-coated by using a solution which contains 5 parts by weight of hydrous crystalline maltotetraosyl glucoside powder obtained by the method in Example A-2, 40 parts by weight of crystalline maltitol, 2 parts by weight of pullulan (average molecular weight: 200,000), 30 parts by weight of water, 25 parts by weight of talc and 3 parts by weight of titanium oxide until the tablet weight was increased to about 230 mg, and further sugar-coated by the solution which contains 10 parts by weight of the above crystalline maltotetraosyl glucoside powder, 55 parts by weight of crystalline maltitol, 1 part by weight of pullulan and 34 parts by weight of water, and glossed with a polishing wax to obtain a sugar coated tablet having a glossy appearance.

The product is excellent in efficiency for sugar-coating process and impact-resistant, and remains its high quality over an extended shortage.

EXAMPLE B-10

Milky lotion

One half parts by weight of polyoxyethylene behenyl ether, 1 part by weight of polyoxyethylene sorbitol tetraoleate, 1 part by weight of oil-soluble glycerol monostearate, 0.5 parts by weight of behenyl alcohol, 1 part by weight of avocado oil, 1 part by weight of a powder containing hydrous crystalline maltotetraosyl glucoside obtained by the method in Example A-2, 2.5 parts by weight of maltitol, 1 part by weight of α-glycosyl rutin and appropriate amounts of vitamin E and germicidal agent were dissolved in usual manner by heating, and the mixture was admixed with 5 parts by weight of 1,3-butylene glycol, 0.1 part by weight of carboxyvinyl polymer and 85.3 parts by weight of refined water and emulsified with homogenizer to obtain milky lotion.

The product is a moisture-retaining milky lotion which is favorably usable as sunscreening agent and skin-whitening agent.

EXAMPLE B-11

Skin cream

Two parts by weight of polyoxylethyleneglycol monostearate, 5 parts by weight of self-emulsifying glycerine monostearate, 2 parts by weight of a-glycosyl rutin, 1 part by weight of liquid paraffin, 10 parts by weight of glycerl trioctanate, 1 part by weight of hydrous crystalline maltotetraosyl glucoside obtained by the method in Example A-1, 3 parts by weight of maltitol and an appropriate amount of antiseptic were dissolved in usual manner by heating, and the resultant solution was admixed with 5 parts by weight of 1,3-butylene glycol and 66 parts by weight of refined water, emulsified with homogenizer and admixed with an appropriate amount of flavoring agent by stirring to obtain skin cream.

The product is a well-spreading cream which is favorably usable as sunscreening cream, skin-refining agent and skin-whitening agent.

EXAMPLE B-12

Dentifrice

Forty-five parts by weight of calcium hydrogen phosphate, 1.5 parts by weight of sodium laurate, 25 parts by weight of glycerine, 0.5 parts by weight of polyoxyethylene sorbitan laurate, 2 parts by weight of a powder containing hydrous crystalline maltotetraosyl glucoside obtained by the method in Example A-3, 3 parts by weight of pullulan, 10 parts by weight of maltitol, 0.02 parts by weight of saccharin and 0.05 parts by weight of antiseptic were admixed with 13 parts by weight of water to obtain dentifrice.

The product, having a superior gloss and detergency, is suitable as dentifrice.

EXAMPLE B-13

Fertilizer rod

Fertilizer composition (N=14%, $P_2O_5$=8%, $K_2O$=12%), pullulan, a powder containing hydrous crystalline maltotetraosyl glucoside obtained by the method in Example A-3, calcium sulfate and water were mixed in the weight of 70, 5, 5, 15 and 5 respectively, and the resultant mixture was fed to an extruder (L/D=20, suppress ratio=1.8, dice diameter= 30 mm) while heating at 80° C. to obtain fertilizer rod.

The product is handleable without vessel for fertilizer and has an appropriate hardness for a total layer application, and can be adjusted its melting speed by arranging the composition ratio. If necessary, the product can be readily admixed with plant hormones, agricultural chemicals and soil conditioners.

As evident from the above description, the crystalline maltotetraosyl glucoside of this invention is a substance which has been unknown conventionally, is non-reducing, less hygroscopic, stable and readily handleable, different from reducing maltopentaose. Further since the crystalline maltotetraosyl glucoside of this invention can be readily separated and purified, the production of crystalline maltotetraosyl glucoside is feasible on the inexpensiveness.

The crystalline maltotetraosyl glucoside is favorably usable as a reagent, substrate for assaying amylase in serum and chemical material, and favorably utilizable in the production of various compositions including foods, beverages, cosmetics, pharmaceuticals. Thus the establishment of crystalline maltotetraosyl glucoside according to this invention and its production and use would have an industrial significance in relevant industries.

While there has been described what is at present considered to be the preferred embodiments of the invention, it will be understood the various modifications may be made therein, and it is intended to cover in the appended claims all such modifications as fall within the true spirits and scope of the invention.

We claim:

1. A non-reducing crystalline maltotetraosyl glucoside selected from the group consisting of a hydrous crystalline maltotetraosyl glucoside and an anhydrous crystalline maltotetraosyl glucoside, wherein:

(a) said hydrous crystalline maltotetraosyl glucoside has the largest diffraction angles (2θ) of 12.6°, 21.3°, 22.1°, and 22.8° on powder X-ray diffraction analysis, exhibits two endothermic peaks at 170 to 172° C. and 230 to 233° C. when measured by a differential scanning calorimeter and a purity of at least 99.5; and (b) said anhydrous crystalline maltotetraosyl glucoside has the largest diffraction angles (2θ) of 12.7°, 13.7°, 18.8°, and 23.2° on powder X-ray diffraction analysis, exhibits one endothermic peak at 230 to 233° C. when measured by a differential scanning calorimeter, and a purity of at least 99.5%.

2. A process for preparing crystalline maltotetraosyl glucoside of claim 1, which comprises:

(a) crystallizing maltotetraosyl glucoside from a solution of maltotetraosyl glucoside; and (b) recovering the crystalline maltotetraosyl glucoside.

3. The process of claim 2, wherein said maltotetraosyl glucoside is prepared by exposing an aqueous solution of maltopentaose to the action of a non-reducing saccharide-forming enzyme, or exposing an aqueous solution which contains trehalose and amylaceous substance or which contains a non-reducing saccharide to the action of cyclomaltodextrin glucanotransferase.

4. The process of claim 3, wherein said solution of maltopentaose is prepared by exposing amylaceous substance to the action of α-amylase or a mixture of α-amylase and a starch debranching enzyme.

5. The process of claim 3, wherein said non-reducing saccharide-forming enzyme is capable of forming a non-reducing saccharide from a reducing partial starch hydrolysate.

6. The process of claim 3, wherein said non-reducing saccharide has a trehalose structure as an end unit.

7. The process of claim 5, wherein said non-reducing saccharide has a trehalose structure as an end unit.

8. The process of claim 5, wherein said reducing partial starch hydrolysate has a glucose polymerization degree of 3 or higher.

9. A process for preparing crystalline maltotetraosyl glucoside of claim 1, which comprises:

(a) alkali-treating an aqueous solution of maltotetraosyl glucoside; and (b) applying the resultant solution to a chromatography to obtain a fraction which is rich in the maltotetraosyl glucoside; and (c) concentrating and crystallizing the fraction; and (d) recovering the crystalline maltotetraosyl glucoside.

10. The process of claim 9, wherein said solution of maltotetraosyl glucoside is obtained by exposing an aqueous solution of maltopentaose to the action of a non-reducing saccharide-forming enzyme, or exposing an aqueous solution which contains trehalose and amylaceous substances or which contains a non-reducing saccharide to the action of cyclomaltodextrin glucanotransferase.

11. The process of claim 10, wherein said solution of maltopentaose is prepared by exposing amylaceous substance to the action of α-amylase or a mixture of α-amylase and a starch debranching enzyme.

12. The process of claim 10, wherein said non-reducing saccharide-forming enzyme is capable of forming a non-reducing saccharide from a reducing partial starch hydrolysate.

13. The process of claim 10, wherein said non-reducing saccharide has a trehalose structure as an end unit.

14. A composition which contains a crystalline maltotetraosyl glucoside of claim 1 and a filler, vehicle, or binder.

15. The composition of claim 14, wherein said composition contains said crystalline maltotetraosyl glucoside in an amount of 0.1 w/w % or more, on a dry solid basis.

16. The composition of claim 14, wherein said composition is in the form of a food, beverage, cosmetic, pharmaceutical or shaped body.

17. A process for preparing a composition containing a crystalline maltotetraosyl glucoside, which comprises a step of incorporating said crystalline maltotetraosyl glucoside into a material for a product selected from the group consisting of foods, beverages, cosmetics, pharmaceuticals and shaped bodies.

18. The process of claim 17, wherein said composition contains said crystalline maltotetraosyl glucoside in an amount of 0.1 w/w % or more, on a dry solid basis.

19. The process of claim 17, wherein said composition is in the form of a food, beverage, cosmetic, pharmaceutical or shaped body.

* * * * *